US 6,714,913 B2

(12) United States Patent
Brandt et al.

(10) Patent No.: US 6,714,913 B2
(45) Date of Patent: Mar. 30, 2004

(54) SYSTEM AND USER INTERFACE FOR PROCESSING TASK SCHEDULE INFORMATION

(75) Inventors: Samuel I. Brandt, Malvern, PA (US); Jan DeHaan, Downington, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 58 days.

(21) Appl. No.: 10/114,218

(22) Filed: Apr. 2, 2002

(65) Prior Publication Data

US 2003/0045958 A1 Mar. 6, 2003

Related U.S. Application Data

(60) Provisional application No. 60/316,604, filed on Aug. 31, 2001.

(51) Int. Cl.[7] .............................................. G06F 17/60
(52) U.S. Cl. ................ 705/2; 705/3; 705/9; 700/101
(58) Field of Search ................... 705/2, 3, 9; 700/101

(56) References Cited

U.S. PATENT DOCUMENTS

| | | | | | |
|---|---|---|---|---|---|
| 4,847,764 | A | * | 7/1989 | Halvorson | 700/231 |
| 5,530,861 | A | | 6/1996 | Diamant et al. | 395/650 |
| 5,692,125 | A | * | 11/1997 | Schloss et al. | 705/9 |
| 5,745,901 | A | | 4/1998 | Entner et al. | 707/103 |
| 5,799,297 | A | | 8/1998 | Goodridge et al. | 707/1 |
| 5,842,173 | A | * | 11/1998 | Strum et al. | 705/1 |
| 5,842,976 | A | * | 12/1998 | Williamson | 600/300 |
| 5,937,388 | A | | 8/1999 | Davis et al. | 705/8 |
| 5,987,422 | A | | 11/1999 | Buzaski | 705/9 |
| 6,052,684 | A | | 4/2000 | Du | 707/8 |
| 6,061,506 | A | * | 5/2000 | Wollaston et al. | 703/23 |
| 6,067,548 | A | | 5/2000 | Cheng | 707/103 |
| 6,078,982 | A | | 6/2000 | Du et al. | 710/200 |
| 6,088,679 | A | * | 7/2000 | Barkley | 705/8 |
| 6,115,646 | A | | 9/2000 | Fiszman et al. | 700/181 |
| 6,278,901 | B1 | | 8/2001 | Winner et al. | 700/99 |
| 6,279,009 | B1 | | 8/2001 | Smirnov et al. | 707/103 |
| 6,308,163 | B1 | | 10/2001 | Du et al. | 705/8 |
| 6,458,080 | B1 | * | 10/2002 | Brown et al. | 600/300 |

OTHER PUBLICATIONS

Georgakopoulos D. et al.,: "An Overview of Workflow Management: From Process Modeling to Workflow Automation Infrastructure," Distributed and Parallel Databases, Kluwer, NL, vol. 3, No. 2, Apr. 1995, pp. 119–153, XP00105525 ISSN: 0926–8682, p. 134–p. 136.
International Search Report.

* cited by examiner

*Primary Examiner*—Leo Picard
*Assistant Examiner*—Michael D. Masinick
(74) *Attorney, Agent, or Firm*—Alexander J. Burke (57) ABSTRACT

A method for providing a displayable task schedule of tasks to be performed on behalf of specific service tasks such as individuals by a particular worker of a plurality of workers is disclosed. In an embodiment, the method comprises receiving worker identification information; compiling a list of tasks to be performed by a worker in response to the received identification information based on a continuing role assigned to the worker and a list of service tasks; and initiating display of the compiled list of tasks.

29 Claims, 4 Drawing Sheets

SYSTEM AND USER INTERFACE FOR PROCESSING TASK SCHEDULE INFORMATION

PRIORITY

This application claims priority through U.S. Provisional Application No. 60/316,604 filed Aug. 31, 2001 for "A System And User Interface For Processing Task Schedule Information."

FIELD OF THE INVENTION

The present invention relates to project management systems in general. More specifically, the present invention relates to mechanisms for reconciling complex and overlapping responsibilities for complex tasks such as those found in a healthcare environment with task allocation models that may be supported by workflow engines. However, the present invention is equally applicable in other industries where complex task allocation is required.

BACKGROUND OF THE INVENTION

Prior art workflow engines permit manipulation of workflow processes, including defining individual work steps to be allocated to systems, individuals, groups of individuals or systems, or combinations thereof. For work steps delegated to systems, individuals, or groups, a desired task description is typically placed into a destination work list, e.g. a set of tasks to be accomplished, at least in part, by or for that system, individual, or group. Destination work lists may be defined at the time that the workflow process definition is created.

Work steps are typically placed into a specific destination work list in response to an event such as the completion of a previous work step or the reception of a system message, rather than when an individual or system is ready to carry out the task associated with that work step.

Prior art workflow models are insufficient for a complex industry such as healthcare. By way of example, in a healthcare system a task such as "dispense medication" may be defined within a workflow process named "medication administration." However, at the time that the workflow process is defined, several degrees of uncertainty may exist including specifics regarding medication, a patient to whom the medication will be administered, a time when the administration is due, and the person who will be responsible at that time for administering the medication. It is preferable that a single process definition should be applicable to all instances of the process, e.g. a drug administration definition should be applicable to the administration of Drug A by nurse Jones on 4 West to patient Smith as well as the administration of Drug B by nurse Galloway to patient McCall on 3 South.

Additionally, in healthcare many individuals may share responsibility for a single service task, and therefore it may be necessary to view the same service task within multiple work lists. For example, nurse Galloway may be on a team with two other nurses. While each nurse on the team may have primary responsibility for a select group of patients, the other two may have secondary responsibility to perform service tasks for those patients if the first nurse, e.g. Galloway, is not available. Therefore, all three nurses may need to see overlapping work items on their own work lists, although these items may need to be presented differently depending on whether the nurse has primary or secondary responsibility. Additionally, a head floor nurse, prior to assigning a new admission, may need to see all of her subordinate nurses' pending tasks.

Prior art workflow engines require an explicit association of work steps and work lists at the time a process is designed. Further, each prior art work step is typically delegated to its associated work list when a system event occurs, not when an individual or system is ready to carry out the service task associated with that work step. This mechanism is inadequate for complex industries such as healthcare. Using the example above, all medication administration work steps could be assigned to a group of nurses who may use a descriptor such as "floor nurse." If a separate group were assigned for each nursing floor, then a separate workflow process would have to be defined for medication administration for each nursing unit. Even then, all of the nurses on each nursing floor would be exposed to all of the patients' service tasks, and there would be no mechanism to explicitly assign service tasks to an appropriate, responsible nurse. Instead each nurse would have to search through the entire ward's nursing tasks to find her own.

Some prior art systems allow for administrative oversight of running tasks, with the ability to manually reassign responsibility for a service task from one individual to another. However, the volume and complexity of doing this in a healthcare setting makes it impractical. By way of example and not limitation, role assignment in healthcare may require that each of the following occur independently: optimal processes are configured, workers are assigned roles (by way of example, IV nurse, floor nurse), roles are correlated with service tasks, and workers assume responsibility for patients. All of these factors taken in concert may determine the appropriate individual responsibility for the performance of a task.

Additionally, some prior art workflow systems allow work items to be delegated to a "role." This allows a service task to be assigned to an individual who will satisfy a role before the process instance is run. By way of example, this can support task delegation to an "officer of the day," as a different officer could assume the role each day. However, this is also not sufficient for healthcare. By way of example, the responsibility for performing a task is not only related to which nurses will be working on "4 West" on a given day and on a given shift, but also upon which patients will be admitted and which nurses will have direct responsibility for which patients. Therefore, it is not possible at workflow process design time to determine which role the task needs to be delegated to.

SUMMARY

The present invention comprises a method for providing a displayable schedule of service tasks to be performed by a particular worker of a plurality of workers, e.g. tasks to be undertaken for or on behalf of specific individuals or objects such as products, equipment, and/or supplies. In an embodiment, the method comprises receiving worker identification information; generating a compilation of service tasks to be performed by the identified worker based on a role or roles assigned to the worker and a list of individuals or objects associated with the worker; and initiating display of the compilation.

In a further embodiment, the method comprises defining roles; defining work step types; creating work steps to be accomplished by workers; mapping work steps to the work step types; mapping work step types to roles; receiving identification information about a worker; assigning at least one role to the worker; generating a record of service tasks to be performed by the worker in response to the received identification information based on the at least one role, the performable tasks' targeted service tasks, and the assigned relationship between the worker and those targeted service tasks; and initiating display of the compiled list of tasks.

The scope of protection is not limited by the summary of an exemplary embodiment set out above, but is only limited by the claims.

BRIEF DESCRIPTION OF THE DRAWINGS

These and other features, aspects, and advantages of the present invention will become more fully apparent from the following description, appended claims, and accompanying drawings in which:

DETAILED DESCRIPTION OF THE PREFERRED EMBODIMENT

The present invention may be used to allocate tasks among one or more appropriate workers in a complicated work environment. In general, throughout this description, if an item is described as implemented in software, it can equally well be implemented as hardware.

Further, as used herein, "user," "worker," and "entity" are understood to interchangeably comprise a individual user or worker, a group or category of users or workers, a role or characteristic of one or more users or workers or groups, and/or a particular device or system such as a medical device or system. As used herein, a "service task," i.e. service task 12, comprises actions to be undertaken by or on the behalf of a worker, e.g. "4" in FIG. 1, or, in healthcare systems, a patient or both as well as items needed to satisfy a requirement for which worker 4 is responsible. For example, in a healthcare environment, service task 12 may include items associated with patient care needs, including the patient himself or herself, by way of example including: a physician order and its associated data; administration of laboratory tests and data associated with the laboratory tests; data associated with patient billing; therapy plans and actual therapy; medication administration and the medication, e.g. pills, shots, or bandaging; and the like; and combinations thereof. It is also understood that although a healthcare clinical information system is used as an exemplary system for illustration purposes, the present invention is applicable to systems involving processing of sequential tasks including in vertical markets in which a workflow engine is embedded within an OEM computer system.

As further used herein, "record" is used herein to signify information or data material to a particular subject where the information or data are preserved in non-volatile, permanent, or tangible form such as in a computer file, disk, CDROM, DVD, or other electronic storage, or the like, or combinations thereof, that are accessible by a computer or other electronic or data processing system.

Figure 1:
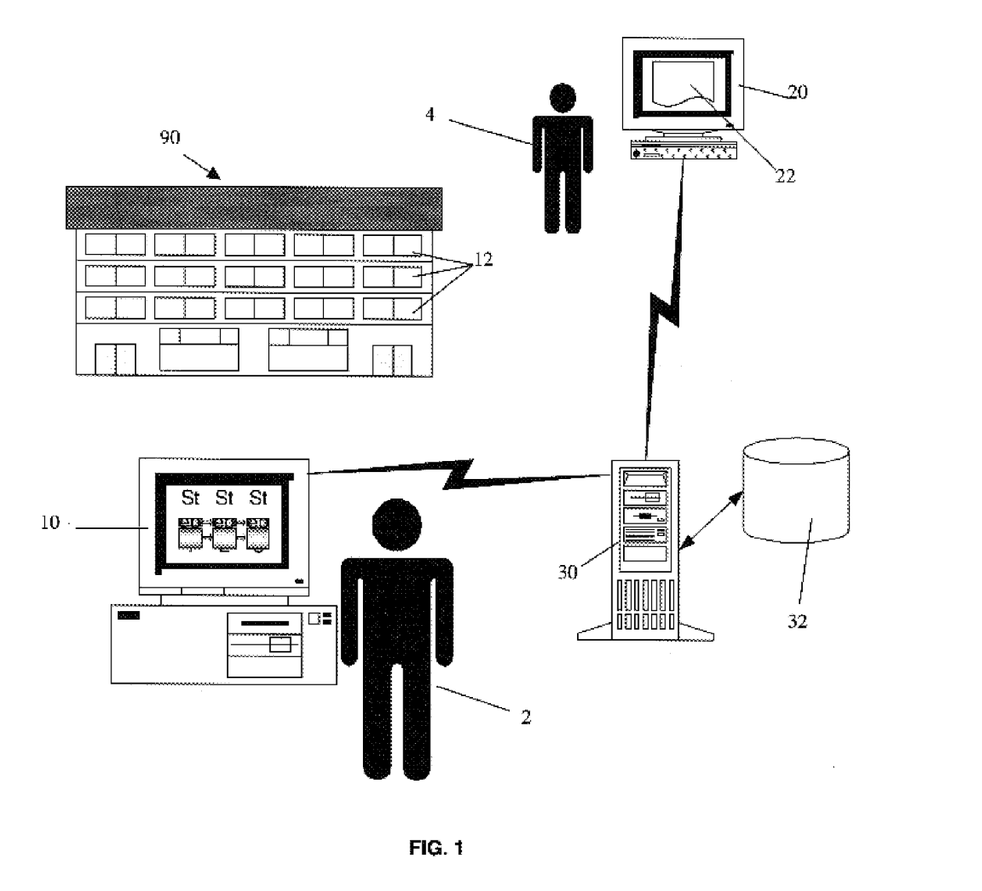
FIG. 1 is a schematic of an exemplary system embodiment.

Referring now to FIG. 1, a schematic overview of a workflow system embodiment of the present invention, the present invention provides a solution for embedding workflow engine technology within a comprehensive vertical software system in an OEM fashion. Although prior art workflow systems have ways to access work list items, additional useful ways may be desired to access work list items. For example, it may be desirable to access all of the individual work steps relating to a specific patient, constituting that patient's activity plan; all of the medication administration work steps for a specific patient, constituting that patient's medication administration record; and/or all of the medication administration work steps for all of a specific nurse's assigned patients, representing that nurse's medication administration task list. The inventors have recognized that it is advantageous to provide this kind of work list flexibility within healthcare in which tasks are assigned to individuals based upon dynamic, complex formulae. In an exemplary embodiment, a system for creating work flows according to the present invention comprises first computer 10 useful in designing and modifying a desired workflow process; second computer 20 where second computer 20 is operatively in communication with first computer 10; and third computer 30 where first computer 10 is operatively in communication with third computer 30. Third computer 30 may act as a server and comprise a workflow engine (not shown in the figures) and database 32. User 2, if user 2 has the authority to design and modify a workflow process, may use first computer 10 to access third computer 30 to create, modify, and manipulate workflow process definitions 22 and work list views 40 (FIG. 2) to create a work step to be performed by worker 4 and the work list view 40 in which it is rendered. Worker 4 may use second computer 20 to access the system and receive a work list 22 tailored for that worker 4. Accordingly, both first computer 10 and second computer 20 comprise input devices (not specifically shown in the figures) such as for entering data, e.g. identification of worker 4, and output devices such as for displaying work lists 22. As will be understood by those in the art, the input device may include a keyboard, a mouse, a biometric device, a card or badge reader, or the like, or combinations thereof. Similarly, the output device may include a display screen, a printer, a pager, a cell phone, a facsimile machine, or the like, a combination thereof.

Computer 10 is useful to allow user 2 with appropriate rights to design and modify a workflow. Computer 10 communicates with a workflow engine (not shown in the figures) executing in a computer such as third computer 30 having access to a database such as 32.

Once implemented, the present invention allows user 2 with appropriate rights to create, modify, and manipulate workflow process definitions 22 and work list views 40 (FIG. 2) such as by mapping work item types, e.g. specific work tasks, to one or more general characteristics of one or more workers 4 who will execute the tasks defined in the workflow design, e.g. service task 12. Additionally, a worker role 26 (FIG. 3) may be represented in the system by a generic code for a "virtual" role 27 (FIG. 3), i.e. a placeholder to be satisfied in real-time by a code representing a specific worker 4. As used herein, a "role" 26, 27 may comprise a task, office, or job description for which a workflow administrator may wish to assign a work item, for example in a healthcare environment comprising nursing roles, administrative roles, physician roles, physician assistant roles, therapist roles, technician roles, and the like, or combinations thereof.

As described more fully below and as will be familiar to those of ordinary skill in the database arts, work list view 40 may be defined by a relationship between one or more tables in one or more databases that can be manipulated programmatically. Work lists 22 and work list views 40 (FIG. 2) may be associated with work flows, such as for institution 90, that relate workers 4 to service tasks 12 and that may be the end result of work-related assignments for institution 90, e.g. patient requirements such as medication to be taken, meals to be provided, drugs to be administered, or therapy to be administered, or the like, or combinations thereof.

Because the workflow engine may be embedded in a vertical application system, workers 4 may access the features of the present invention through an interface associated with the vertical system. Accordingly, worker 4 may log into a system such as at computer 20 to access vertical system software and, once logged into that vertical system software, view a compiled record comprising work lists 22 associated with worker 4 on a display device, e.g. a display screen, a printer, pager, cell phone, or the like, or a combination thereof. It is understood that computer 10, computer 20 and third computer 30 need not be separate computers but may be a single computer or computer system.

Figure 2:
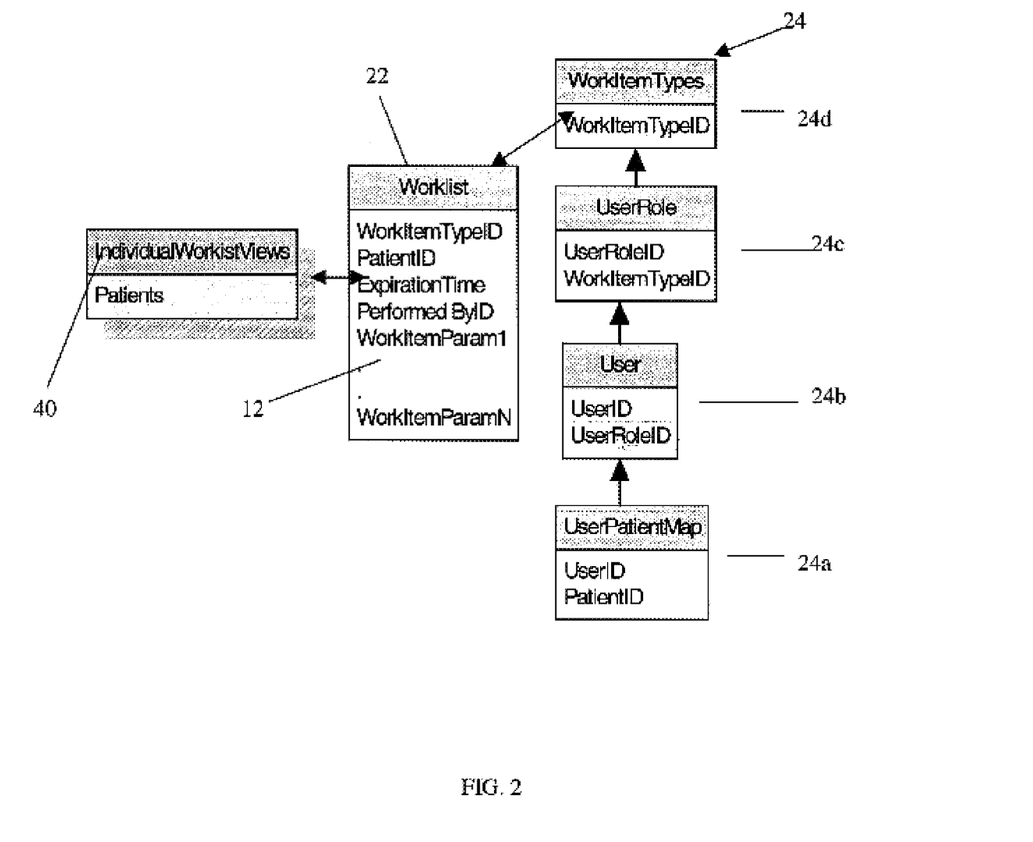
FIG. 2 is a diagrammatic representation of an exemplary work list view and work lists.

Referring additionally to FIG. 2, an object schematic of a work list view, work list 22 may be created by examining worker data objects 24b related to worker 4. In an exemplary embodiment, properties of worker data object 24b may include a user role property, e.g. userRoleID, which contains a value representing an actual user role 26 (FIG. 3) or a virtual role 27 (FIG. 3) that the specific worker 4 can satisfy. Worker data objects 24b may be queried using a unique user role 26 identifier for worker 4 as well as one or more virtual roles 27 that worker 4 may satisfy. For example, worker 4 may satisfy a virtual role 27 for a medication giver as well as a virtual role 27 for a physical therapist but not a virtual role 27 for a medication prescriber.

Work item types may have additional descriptions such as at work step data object 24d. These descriptions and other properties may be related to virtual role object 24c such as by a work item type identifier.

In this exemplary health care example, a patient may be dynamically associated with worker 4 in real-time, such as shown at patient data object 24a. For example, patient data object 24a may relate an actual patient with a specific worker 4. Patients may additionally have needs or requirements directly or indirectly associated with those patients which one or more workers 4 need to address as part of a work assignment for worker 4.

One or more service tasks 12 will be retrievable based on worker data object 24b that is related into role data object 24c such as by the identifier of worker 4. Work list 22 may then be created based using the patient data and data for worker 4.

Each work list 22 may further comprise a task identifier as well as an identifier of the responsible worker 4 (FIG. 1) to be assigned the service task. The identifier for worker 4 may be a generic code at creation, e.g. one for a virtual role 27, and filled in with a code representing a specific worker 4 at runtime. Work lists 22 may therefore comprise work item types such as specific work tasks to be mapped to a general user characteristics. Using virtual roles 27, specific workers 4 (FIG. 1) may be associated with one or more virtual roles 27 and then dynamically mapped into a virtual role 27 associated with work list 22 such as at runtime. Thus, virtual role 27 may act as a "place holder" to be satisfied by a specific worker 4 at the time when the task is to be performed. Additionally, one or more characteristics of the task to be performed, e.g. a patient identifier, may also be mapped dynamically to worker 4.

By way of example and not limitation, in an exemplary health care embodiment, a virtual role 27 may be associated with a predetermined type of work step. The actual work step, e.g. a step to effect a specific service task 12, may, in turn, also be associated with a predetermined work step type. Further, both workers 4 and work steps may be independently associated with patients such as on an individual and/or group basis. Using these associations, worker 4 may be assigned a subset of work steps based upon virtual role 27 and patient associations.

One or more work lists 22 may be accessed through one or more work list views 40. Such work list views 40 may access a single data collection (such compiled records of work lists 22 contained in database 32 in FIG. 1) using numerous methods as will be familiar to those of ordinary skill in the database arts, e.g. SQL joins, filters, and the like.

Figure 4:
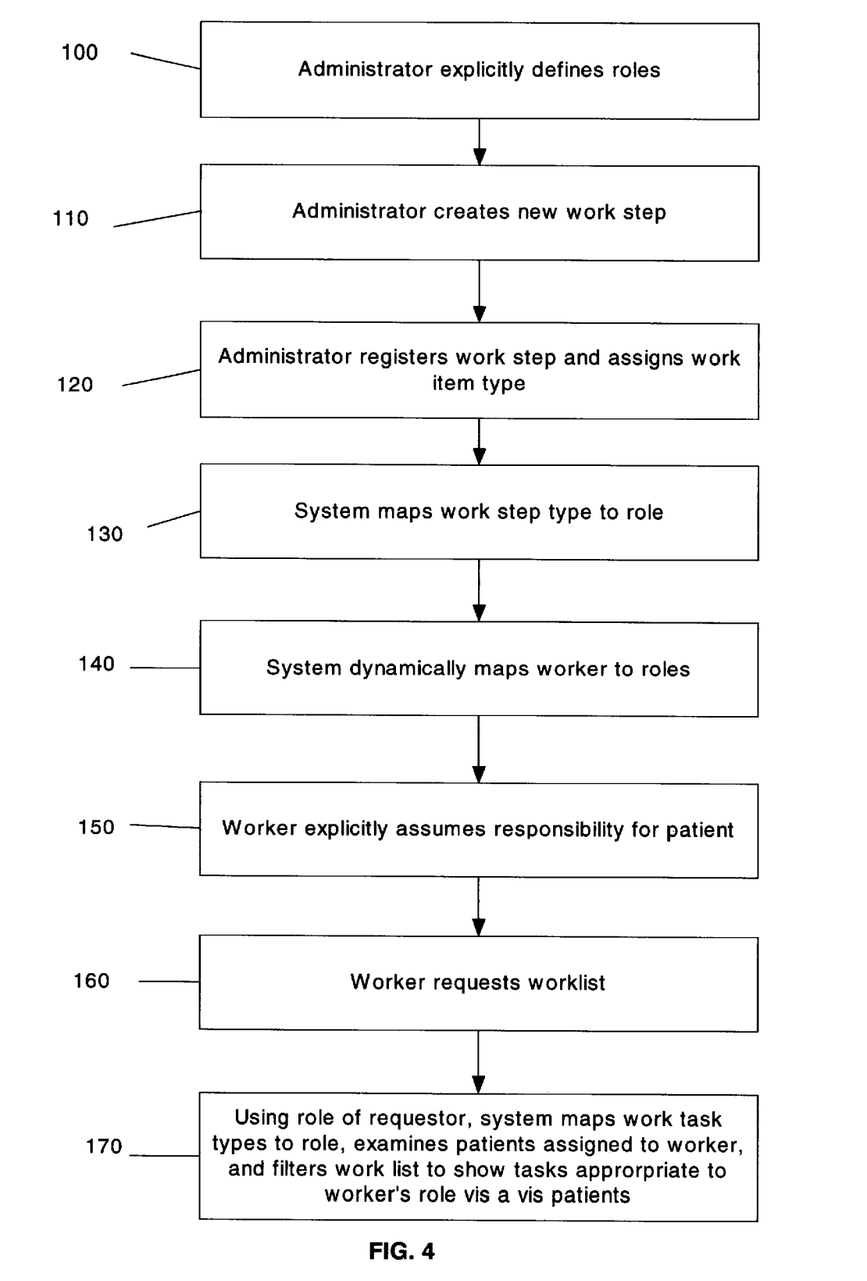
FIG. 4 is a flowchart of an exemplary embodiment the present invention.

In the operation of an exemplary embodiment, referring now to FIG. 4, a flowchart of an exemplary embodiment, a displayable task schedule concerning service tasks 2 to be performed by a particular worker 4 of a plurality of workers 4 is created by receiving identification information reflective of worker 4; compiling a record identifying service tasks 12 to be performed by worker 4 in response to the received identification information and based at least partially on at least one of a role 26 assigned to the worker 4, a service task 12 associated with the identified worker 4, and/or a predetermined relationship between the identified worker 4 and the intended a target beneficiary of the service task 12; and initiating display of the compiled record at a display device. The displayable compiled record may be formatted for display as a schedule of service tasks 12 that may be performed by at least one worker 4 of a plurality of workers 4.

Accordingly, one or more worker roles 26 are defined by user 2 with appropriate authority to define worker roles 26. User 2 with appropriate authority to define work step types also defines one or more work step types. Additionally, user 2 with appropriate authority to create a work step creates a work step to be accomplished by worker 4, and user 2 with appropriate authority to map work steps to work step types maps the work step to a work step type. Each of these users 2 above may be the same user 2 or may be a plurality of users 2, each of whom has differing authority.

Work step types are mapped to worker roles 26, 27. Accordingly, when worker 4 wish to use the present invention, worker 4 provides identification information about the worker 4 which is received into the system, whereupon user role 26 is assigned to worker 4 and a record comprising descriptions of service tasks 12 to be performed by worker 4 in response to the received identification information is compiled, based on the user role 26 assigned to worker 4. The record may then be formatted for display at a display device, e.g. computer 20.

Figure 3:
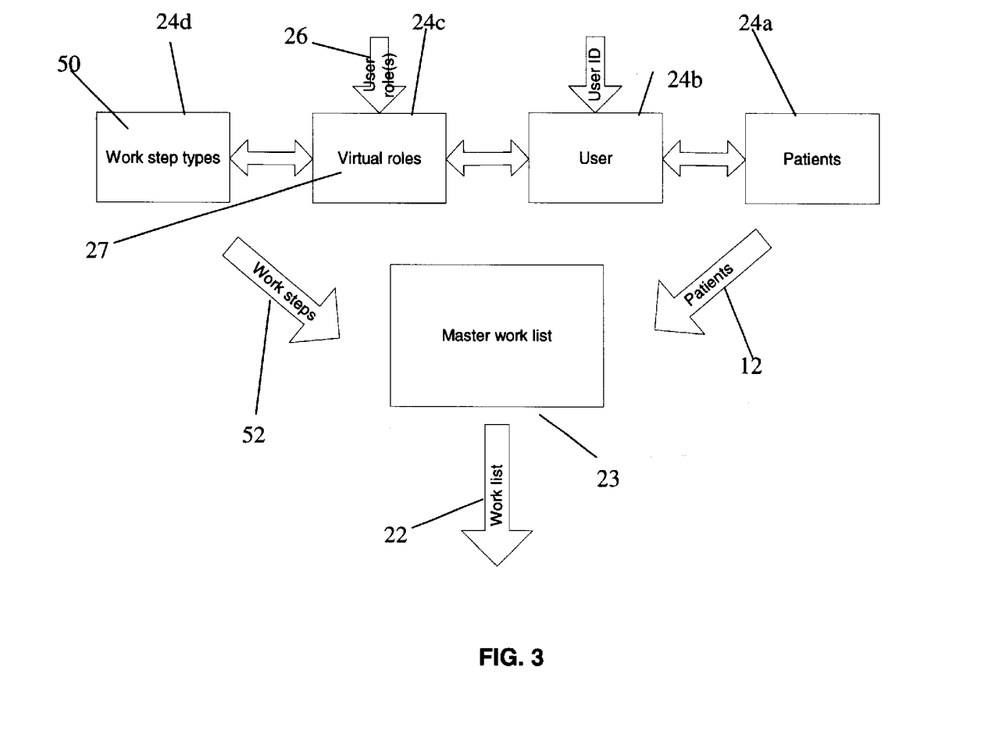
FIG. 3 is a representative relationship flow model of an exemplary of the present invention.

User 2 with appropriate rights, such as an administrator, explicitly defines 100 one or more worker roles 26 (FIG. 3). When a new work step 50 (FIG. 3) is created 110, the new work step 50 is registered and assigned 120 a work item type (not shown in the figures) by the work step definition creator, e.g. user 2. In a currently preferred embodiment, this is an explicit operation required for each new work step 50. By way of example and not limitation, in a typical embodiment, user 2 (FIG. 1) acting as a workflow designer may configure one or more work steps such as "dispense medication" within a process design such as at computer 10 (FIG. 1).

In a currently preferred embodiment, user 2 acting as a workflow designer (shown in FIG. 1) creates workflow processes utilizing work steps 52 (FIG. 3) that have been pre-configured. If workflow designer user 2 identifies a new work step 52, the new work step 52 may be registered with an associated work step type 50. Further, as discussed herein below, when worker 4 signs on and requests work list 22, work list view 40 may be dynamically constructed which matches one or more worker roles 26, 27 associated with a worker 4 to appropriate work steps 52, e.g. for service tasks 12 (FIG. 1) associated with patient requirements. If the workflow engine needs to escalate a task to worker 4, it may examine the work task type and one or more work detail characteristics, e.g. an associated patient ID, and then query for roles 26, 27 associated with the task type. Once the query is answered, a system using an embodiment of the present invention identifies an individual worker 4 associated both with that role 26, 27 and that work detail characteristic.

Workflow engines may be associatable with work flows such as for a target process, e.g. one involving institution 90 (FIG. 1). Accordingly, users 2 may explicitly define roles 26, 27 such as for institution 90 (FIG. 1) and then explicitly map work task types 50 onto these roles 26, 27 either automatically or manually 130. In a preferred embodiment, an automated method of mapping is consistent with manual processes. For example, a new work task type 50 may be defined based upon an existing work task type 50, automatically inheriting the role relationships of the parent work task 50.

By separating the correlation between work steps 50 and roles 26, 27 from a workflow configuration, the present invention allows tasks to be reassigned to accommodate new delivery models without impacting workflow configurations. By way of example and not limitation, an institution 90 (FIG. 1) such as a hospital may implement a new service task 12 such as pulse oximetry. Based upon their roles 26, 27 as well as the relationship(s) between roles 26, 27 and service tasks 12 to be accomplished, hospital 90 decides which workers 4 will be needed to provide service task 12 when it is ordered, e.g. respiratory therapy, nursing, or both. By way of further example and not limitation, when an attending doctor requests work list 22, the doctor (worker 4) may be presented with a list of service tasks 12, e.g. tasks appropriate for that physician, but which are further limited to service tasks 12 for those patients for whom the doctor is then responsible.

Once work steps 50 are defined and assigned, individual workers 4 (FIG. 1) may be dynamically mapped 140 into roles 26, 27 such as by using relational database techniques or object queries. By way of further example, each individual healthcare worker 4 may explicitly assume responsibility 150 for one or more individual service tasks 12 such as patient care responsibility (FIG. 1). However, such responsibilities may be implemented with a single service task 12 such as an item needed to satisfy a patient care requirement; with a group of service tasks 12 such as patient care responsibility for the group; or on an abstraction such as a nursing unit, department, or other level that can be resolved to a group of service tasks 12 such as patient care responsibility for all of the patients contained within the group. Worker 4, e.g. a, doctor or a nurse, may then assume responsibility for a group of service tasks 12 such as at a shift change. Workers 4 may also assume responsibility for a plurality of groups of service tasks 12, e.g. a respiratory therapist may assume responsibility for groups of patient requirements on several floors in hospital 90. Moreover, an individual worker 4 may also assume responsibility such as in an oversight or team capacity. Using virtual roles 27, user roles 26, and other data such as data relating to work steps 50 and service tasks 12 such as patient requirements, the present invention may capture assignment of service tasks 12, create a mapping between patients and workers 4, and use the mapping to present appropriate work items to worker 4. By way of example, in an exemplary hospital embodiment, such mapping may correspond to a nurse signing on to a system of the present invention, e.g. as a "floor nurse" on "4 West" or as an "ICU nurse" in a "surgical ICU" section. Once signed in, the nurse may use a user interface appropriate for both the contextual setting and her role (not shown in the figures) to request 160 a work list 22. By linking the user, e.g. the nurse, to a role 26, e.g. "ICU nurse," the present invention is able to provide appropriate work lists 22 that show those tasks appropriate for that user's role.

When worker 4 requests work list 22 such as at step 160, the present invention may examine 170 the worker role 26 of worker 4 and then map worker 4 to work task types 50 associated with that worker role 26. Such an examination may further entail examining service tasks 12 currently assigned to worker 4 and creating a work list view 40 from master work list 23 (FIG. 3) to show only those tasks appropriate to the worker role 26 of that worker 4 that pertains to service tasks 12 for whom that worker 4 has responsibility.

Once the mapping is completed, the present invention may compile a record identifying or otherwise encapsulating identification of service tasks 12 for worker 4 as work list 22. The compiled work list 22 may comprise service tasks 12 that are currently due and service tasks 12 that are predicted to become due after other service tasks 12 have been completed. Service tasks 12 may be predicted by using (1) all future assignments or requirements specified in a workflow definition that are mapped to certain work types 50 and service tasks 12; (2) only those future assignments or requirements specified in the workflow definition that are mapped to certain work types and service tasks 12 and that will become due when the (previously defined) default conditional alternatives are assumed to become true; and/or (3) only those future tasks specified in the workflow definition that are mapped to certain work types and service tasks 12, and that will become due when the most likely conditional alternatives are assumed to become true.

Accordingly, using the present invention, process design may be isolated from task allocation. Further, systems using the present invention may provide support for multiple dimensions of responsibility for determining task delegation as well as support for explicit assumption of dynamic responsibilities, such as patient care. Further, systems using the present invention may provide support for team based responsibility and multiple levels of oversight. Given its dynamic allocation, systems using the present invention may provide for reallocation of task responsibility, including those tasks in the midst of completion.

In an exemplary embodiment, the present invention is consistent with a complex environment such as healthcare. In healthcare, services are provided to patients. These services are amenable to management with workflow engine technology. Typically, the services require the involvement of many different individuals and many different departments. The services selected, and therefore the work steps required, are chosen based upon the patient's needs. However, in complex work environments, one or more particular workers 4 may act in multiple roles. By way of example and not limitation, worker 4 can be a nurse with his or her own group of patients; a nurse who is a member of a team, seeing work tasks for her team member's patients; and/or a head nurse, viewing all of the tasks for her subordinate nurses' patients. The flexibility allows a work list 22 to be constructed based upon the multiple factors inherent in complex environment such as healthcare. It also permits the development of complex work lists 22 which are assembled from multiple views 40 and which can render items from different views 40 in an easily recognizable manner. For example, a nurse who is a member of the nursing team could have the work items for her own patients rendered in bold, and those of her team members in italics. This may be accomplished by numerous equivalent means, such as by dynamically creating a work list 22 based upon the correlation between the user's role(s), user's patient responsibilities, the work items, and the targeted patients.

Workflow engines can provide coordination of many constituent work steps. However, in some situations various entities such as departments or group supervisors tasked with fulfilling the service requests choose which individuals will perform them. This creates a far more flexible system, comprising:

Support for dynamic reallocation of responsibilities;

Provision for multilevel, team based task assignment;

Allowing work list items to be viewed in multiple different contexts; and

The present invention further provides a mechanism for designing workflow processes in healthcare in a generic fashion, while supporting their specific implementation.

FIG. 3 is a schematic flow of an embodiment showing relationships between certain components of the present invention. Referring additionally to FIG. 1, in an exemplary embodiment, in response to the received identification information, the system, using the workflow engine, compiles a record that includes a list of service tasks 12 to be performed by worker 4. Compiled records may be used to provide work list 22 that is also based at least partially on one or more worker roles 26, 27 and a list of service tasks 12 associated with worker 4. Once the record is compiled, display of the compiled work list 22 may be initiated at a display device for worker 4.

As shown additionally in FIG. 2 and discussed above, relationships between work item data object 24d, role data object 24c, worker data object 24b, and patient data object 24a allow creation of work list 22 for a worker 4 from the compiled record. Additionally, actual work steps 52 may also be defined using work step types 50 encapsulated in work step data object 24d. For example, patient requirements 12 may be retrieved from patient data object 24a and merged into a master work list 23, e.g. at database 32 (FIG. 1). Once created, master work list 23 may then be manipulated such as by using work list views 40 to create a set of tasks tailored to worker 4. This allows the same work list item to be viewed in many different contexts, such as those pertaining to team nursing described above.

Accordingly, a displayable task schedule comprising one or more activities to be performed on or for one or more specific, service tasks 12 by a particular worker 4 (FIG. 1) may be created and manipulated. In part, the present invention may be used to provide separation between workflow process design and task delegation logic, and permit workflow processes to be configured based upon their optimal performance without requiring direct knowledge of the individual workers 4 who will ultimately perform the tasks, at the time the process is defined and the workflow task is designed.

In an exemplary embodiment, the present invention separates the tasks of workflow process design from those tasks entailed in assigning responsibility to individuals. Workflow designer 2 may configure the work step without prior knowledge of the individual, role, group or skill who will ultimately be assigned to perform the task, e.g. worker 4. In one embodiment, the responsibility for performing the task may be assigned at task execution time.

It will be understood that various changes in the details, materials, and arrangements of the parts which have been described and illustrated above in order to explain the nature of this invention may be made by those skilled in the art without departing from the principle and scope of the invention as recited in the following claims.

What is claimed is:

1. A processing system for providing a displayable task schedule of at least one service task to be performed by at least one worker, comprising:

an input processor for receiving worker identification information;

a repository associating a worker with a role to be performed by the worker and with a plurality of service tasks to be performed for a plurality of task beneficiaries and with a subset of the plurality of service tasks to be performed by the worker for a particular beneficiary of the subset of service tasks;

a data processor for automated compiling of a record using information derived from the repository in response to the received worker identification information and a worker initiated command to access selected information, the compiled record including items identifying, (a) individual tasks of the subset of service tasks, (b) the particular beneficiary of the subset of service tasks and (c) the worker performing the subset of service tasks; and a display generator for initiating generation of data representing a display image presenting the compiled record.

2. The system of claim 1, wherein in response a second worker initiated command, the data processor compiles a second record including items identifying, (i) the worker and (ii) the plurality of service tasks to be performed for the plurality of task beneficiaries and the service task is at least one of (a) a physician order, (b) administration of laboratory or other diagnostic tests, (c) therapy plans, (d) therapy services administration, (e) medication administration, and (f) medication administration plans.

3. The system of claim 1, wherein the compiled record includes an item identifying the role performed by the worker and a role comprises at least one of (a) a nursing role, (b) an administrative role, (c) a physician role, (d) a physician assistant role, (e) a therapist role, (f) a technician role, and (g) a role assigned by a workflow administrator.

4. The system of claim 1, wherein the role assigned to the worker comprises a role performable by more than one worker of a predetermined plurality of workers.

5. The system of claim 1 wherein:

the repository associates multiple workers comprising a multilevel team with the role, the role comprises a team-based task assignment and the data processor automatically re-assigns a service task to be performed by the worker to another worker of the team in response to unavailability of the worker and avoiding re-scheduling of the service task.

6. The system of claim 4 wherein the service task to be performed by the worker is re-assigned to another worker of the predetermined plurality of workers in response to unavailability of the worker and avoiding re-scheduling of the service task.

7. The system of claim 1 wherein the role assigned to the worker comprises a task characteristic associated with at least one of, (a) a predetermined characteristic of a work step and (b) a service task and the work step includes at least one of (i) a work step to be performed by a first user and (ii) a work step to be performed by a second user for whom the first user has a supervisory responsibility.

8. The system of claim 1 wherein the repository comprises at least one database and the data processor automatically compiles the record.

9. The system of claim 1 wherein the data processor compiles the record by using a view of service tasks, the view reflecting a predetermined image sequence navigation context identifying the information required in response to the command to access selected information.

10. The system of claim 1 wherein the compiled record further indicates who is currently responsible for executing a predetermined service task based on current assignment of roles and current association with service tasks.

11. The system of claim 1 wherein the service tasks comprise at least one of (a) a service required by a beneficiary, (b) providing a product, (c) providing a supply, and (d) providing equipment.

12. The system of claim 11 wherein a beneficiary comprises at least one of, (a) a medical patient-and (b) an organization.

13. The system of claim 1, wherein the service task further comprises a work step and the repository associates the work step with a work step type and with the particular beneficiary and the compiled record includes an item identifying a work step type.

14. The system of claim 13, wherein in response a second worker initiated command, a second compiled record includes items identifying,
  (i) the role and
  (ii) the plurality of service tasks to be performed for the plurality of task beneficiaries by a worker performing the role.

15. The system of claim 1 wherein the repository associates service task type with a service task and the data processor dynamically reallocates service tasks associated with the worker to another worker in response to a determined service task type.

16. A computer program embodied within a computer-readable medium created to perform the steps of the system of claim 1.

17. A processing system implemented method for providing a displayable task schedule of a service task to be performed by at least one worker of a plurality of workers, comprising the activities of:

defining a worker role by a user with appropriate authority to define the worker role;

creating a work step to be accomplished by the at least one worker by a user with appropriate authority to create a work step of a particular type;

mapping the work step type to the worker role;

receiving identification information identifying the at least one worker;

assigning the worker role to the at least one worker;

deriving information from a repository associating the worker with the assigned role to be performed by the worker and with a plurality of service tasks to be performed for a plurality of task beneficiaries and with a subset of the plurality of service tasks to be performed by the assigned worker for a particular beneficiary of the subset of service tasks; and using derived information in generating data representing at least one image, in response to a user initiated command to access selected information, the at least one image including items identifying,
  (a) individual tasks of the subset of service tasks,
  (b) the particular beneficiary of the subset of service tasks and
  (c) the assigned worker performing the subset of service tasks.

18. A processing system for providing a displayable task schedule of at least one service task to be performed by at least one worker, comprising:

a repository associating a worker with a role to be performed by the worker and with a plurality of service tasks to be performed for a plurality of task beneficiaries and with a subset of the plurality of service tasks to be performed by the worker for a particular beneficiary of the subset of service tasks;

a data processor for using information derived from the repository in adaptively generating data representing at least one image, in response to a worker initiated command to access selected information, the at least one image including at least two of the items identifying,
  (a) individual tasks of the subset of service tasks,
  (b) the particular beneficiary of the subset of service tasks
  (c) the worker performing the subset of service tasks;
  (d) the worker and
  (e) the plurality of service tasks to be performed for the plurality of task beneficiaries.

19. The method of claim 17 including the activities of:

mapping work task types to the worker role;

examining additional criteria useful for filtering work task types;

creating a view of a master work list, the view based at least partially on a context comprising the work task types mapped to the worker role and the additional criteria; and creating a display of the compiled record using the view.

20. The method of claim 19 wherein the additional criteria comprise a list of service tasks associated with the worker.

21. The method of claim 17, wherein the worker role assigned to the worker comprises a role performable by multiple workers.

22. The method of claim 17 wherein the compiled record comprises service tasks that are currently due and service tasks that are predicted to become due after other service tasks have been completed.

23. The method of claim 22 wherein
the predicted tasks are predicted by at least one of:
including a predetermined number of future tasks specified in a definition of the workflow that are mapped to predetermined work types and service tasks;
including only predetermined future tasks specified in the workflow definition that are mapped to certain work types and service tasks and that will become due when the default conditional alternatives are assumed to become true; and
including only predetermined future tasks specified in the workflow definition that are mapped to certain work types and service tasks, and that will become due when the most likely conditional alternatives are assumed to become true.

24. The method of claim 17 including the activity of
defining a work step type by a user with appropriate authority to define work step types.

25. A system for creating work flows, comprising:
a first computer, comprising:
a workflow engine; and
a database associating a worker with a role to be performed by the worker and with a plurality of service tasks to be performed for a plurality of task beneficiaries and with a subset of the plurality of service tasks to be performed by the worker for a particular beneficiary of the subset of service tasks;
a second computer for use in determination and modification of a workflow process, the second computer being operatively in communication with the first computer; and
a third computer including an input device for entering identification about a worker and an output device for displaying a work list indicating work tasks to be performed; wherein
a user with authority to design and modify a workflow process may use the second computer to access the first computer to create, modify, and manipulate work lists and work list views to create a work step to be performed by the worker; and
in response to a worker initiated command to access selected information, the third computer uses information derived from the database in generating data representing at least one image, the at least one image including items identifying,
(a) individual tasks of the subset of service tasks,
(b) the particular beneficiary of the subset of service tasks and
(c) the worker performing the subset of service tasks.

26. The system of claim 25 wherein
a computer comprises at least one of, (a) a processor, (b) a controller and (c) a processing device and
at least two of the first computer, the second computer, and the third computer are the same computer.

27. A processing system for providing a displayable task schedule of at least one service task to be performed by at least one worker, comprising:
an input processor for receiving worker identification information;
a repository associating a worker with a role to be performed by the worker and with a plurality of service tasks to be performed for a plurality of task beneficiaries and with a subset of the plurality of service tasks to be performed by the worker for a particular beneficiary of the subset of service tasks;
a data processor for generating data representing at least one image using information derived from the repository and, in response to the received worker identification information and a worker initiated command to access selected information, the at least one image including items identifying,
(a) individual tasks of the subset of service tasks,
(b) the particular beneficiary of the subset of service tasks and
(c) the worker performing the subset of service tasks.

28. A system according to claim 27, wherein
the data processor uses information derived from the repository in adaptively generating data representing at least one image including items identifying,
(i) the worker and
(ii) the plurality of service tasks to be performed for the plurality of task beneficiaries.

29. A system according to claim 27, wherein
the data processor re-assigns a service task to be performed by the worker to another worker in response to unavailability of the worker and avoiding re-scheduling of the service task.

* * * * *